United States Patent [19]

Stein et al.

[11] 4,167,565
[45] Sep. 11, 1979

[54] ADENOSINE-5'-CARBOXAMIDES AND METHOD OF USE

[75] Inventors: Herman H. Stein, Skokie, Ill.; Raj N. Prasad, Pierrefonds, Canada; Karin R. Tietje, Philipsburg, Canada; Anthony K. L. Fung, Pierrefonds, Canada

[73] Assignee: Abbott Laboratories, North Chicago, Ill.

[21] Appl. No.: 739,684

[22] Filed: Nov. 8, 1976

[51] Int. Cl.² .................... A61K 31/52; C07H 19/16
[52] U.S. Cl. ................................. 424/180; 536/24; 536/26
[58] Field of Search ................. 424/180; 536/26, 24

[56] References Cited

U.S. PATENT DOCUMENTS

| | | | |
|---|---|---|---|
| 3,864,483 | 2/1975 | Stein et al. | 424/180 |
| 4,029,884 | 6/1977 | Stein et al. | 536/24 |

*Primary Examiner*—Johnnie R. Brown
*Attorney, Agent, or Firm*—Robert L. Niblack; Gildo E. Fato

[57] ABSTRACT

A method of controlling undesired animals including rodents, coyotes and birds which comprises making available to said animals an edible composition containing, as the active ingredient, a lethal dose of a compound represented by formula

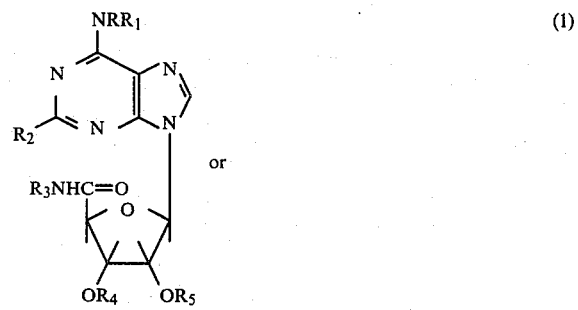

or

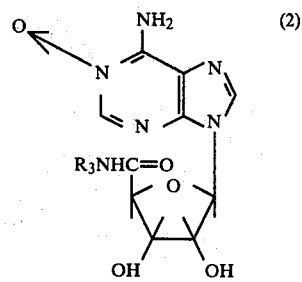

wherein R is H, loweralkyl or acetyl; $R_1$ is H or acetyl; $R_2$ is H, Cl or $NH_2$; $R_3$ is H, loweralkyl, alkoxy, cycloalkyl or hydroxyalkyl; $R_4$ and $R_5$ are each H, acetyl or propionyl, or when taken together form a p-chlorobenzylidene, a carbonate or an ethoxymethylene moiety; in a suitable carrier.

15 Claims, No Drawings

ADENOSINE-5'-CARBOXAMIDES AND METHOD OF USE

BACKGROUND OF THE INVENTION

The present invention relates to undesired animals such as rodents, coyotes and dangerous birds, and lethal drugs used for their control. It is very necessary to have a means which is effective and inexpensive to control these undesired animals.

Undesirable animals, e.g., rodents and particularly rats, are responsible for extensive and serious damage to man's well-being. They are known to consume and contaminate food supplies and to destroy grain fields. In addition, they are known to carry and transmit diseases, to create social nuisances, and to cause damage to buildings. In the United States alone, it is a well-known fact that the annual damage caused by pests results in a loss of hundreds of millions of dollars. It is clear, therefore, that the method of the present invention for the control of undesired animals is a welcomed contribution.

In the past, poison chemicals have been used in the elimination of such unwanted animals. However, such poison chemicals were easily detected or so toxic that the undesirable animals would not ingest a lethal dose. Therefore, it would be advantageous to have a drug or material as provided by the present invention which is lethal to these unwanted animals but still a drug or material is edible by these undesirable animals.

DETAILED DESCRIPTION OF THE INVENTION

The present invention provides a method of controlling undesired animals such as rodents, coyotes and dangerous birds. The method comprises making available to the undesired animals an edible composition containing, as the active component, a lethal dose of a compound represented by the formula

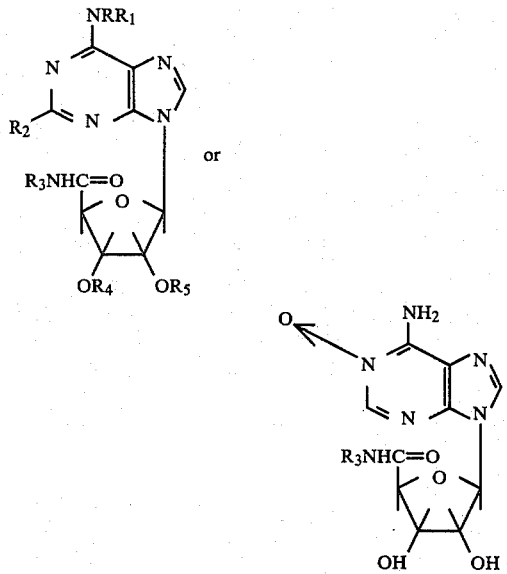

wherein R is H, loweralkyl or acetyl; $R_1$ is H or acetyl; $R_2$ is H, Cl or $NH_2$; $R_3$ is H, loweralkyl, alkoxy, cycloalkyl or hydroxyalkyl; $R_4$ and $R_5$ are each H, acetyl or propionyl, or when taken together form a p-chlorobenzylidene, a carbonate or an ethoxymethylene moiety; and a suitable carrier.

The term "undesired animals", as used herein, refers to undesirable rodents, coyotes and birds which are economically and socially destructive to man. More specifically, the term "undesired animals" refers to undesirable rodents such as rats, mice, ground squirrels, prairie dogs, pocket gophers, rabbits, nutria, and the like; coyotes; and undesirable birds, such as pigeons, starlings, blackbirds, grackles, cowbirds, crows, and the like.

As used herein, the term "loweralkyl" refers to $C_1$–$C_6$ straight or branched chain alkyl groups including methyl, ethyl, n-propyl, iso-propyl, n-butyl, sec-butyl, tert-butyl, n-pentyl, iso-pentyl, neo-pentyl, n-hexyl and the like.

The term "alkoxy" refers to alkoxy groups having a total of no more than 6 carbon atoms such as methoxy, ethoxy, n-propoxy, iso-propoxy and the like.

"Cycloalkyl" as used herein, refers to cyclic saturated aliphatic radicals having three to eight carbon atoms in a ring, such as cyclopropyl, cyclobutyl, cyclopentyl, cyclohexyl, cycloheptyl and cyclooctyl.

The term "hydroxyalkyl" refers to hydroxyalkyl groups having from 1 to 6 carbon atoms, such as hydroxymethyl, hydroxyethyl, hydroxypropyl, hydroxybutyl, hydroxypentyl, hydroxyhexyl and the like.

The present invention includes within its scope lethal compositions comprising, as an active ingredient, at least one of the compounds of this invention in association with an acceptable carrier or diluent.

Liquid dosage forms for oral administration include acceptable emulsions, solutions, suspensions, syrups and elixirs containing inert diluents commonly used in the art, such as water. Besides inert diluents, such compositions can also include adjuvants, such as wetting agents, emulifying and suspending agents and flavoring agents.

The compounds of this invention exhibit a lethal effect on undesired animals at a dose ranging from 1 to 100 mg./kg. body weight. A lethal dose (oral $LD_{50}$) for mice ranges from about 10 to 50 mg./kg.; for rats from 0.5 to 10 mg./kg.; for coyotes from 5.0 to 10 mg./kg.; and for birds from 0.5 to 10 mg./kg.

The present compounds may be prepared by means of various methods and processes. For example, compounds represented by formula 1

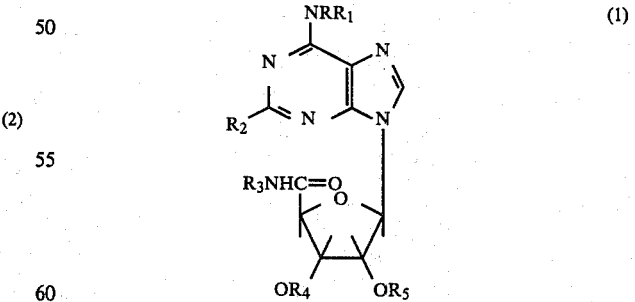

wherein each of R, $R_1$ and $R_2$ is H; $R_3$ is H, alkyl, cycloalkyl or hydroxyalkyl; and each of $R_4$ and $R_5$ is H or acetyl, can be prepared according to the process described in U.S. Pat. 3,864,483. Also, the compounds of formula (1) wherein each of R, $R_1$, $R_2$, R 4 and $R_5$ is H; and $R_3$ is alkoxy, can be prepared according to the method described in U.S. Pat. No. 3,855,206.

Moreover, the preparations of compounds of formula 1 wherein R is H, alkyl or alkoxy; $R_1$ is H or alkyl; $R_2$ is H; $R_3$ is loweralkyl or cycloalkyl; and where each of $R_4$ and $R_5$ is H, alkoxy, or when taken together form a p-chlorobenzylidene, a carbonate or an ethoxymethylene moiety, are described in the Examples herein-below.

In addition, compounds of formula 2

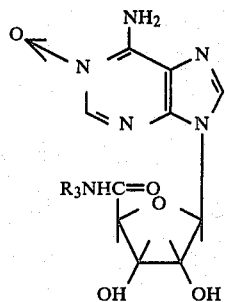

(2)

where $R_3$ is alkyl or cyclopropyl, may be prepared according to the processes described in the Examples herein-below.

According to the present invention, the compounds that are lethally effective against undesired animals include compounds of formula 1:

(3) Adenosine-4'-carboxamide
(4) Adenosine-5'-[(N-methyl)-carboxamide]
(5) Adenosine-5'-[(N-ethyl)-carboxamide]
(6) Adenosine-5'-[(N-isopropyl)-carboxamide]
(7) Adenosine-5'-[(N-cyclopropyl)-carboxamide]
(8) $N^6$-methyl-adenosine-5'-[(N-ethyl)-carboxamide]
(9) $N^6$-methyl-adenosine-5'-[(N-cyclopropyl)-carboxamide] (10) Adenosine-5'-[N-(2-hydroxyethyl)carboxamide]
(11) 2',3'-Diacetyl-adenosine-5'-[(N-cyclopropyl)-carboxamide]
(12) 2',3'-Diacetyl-adenosine-5'-[(N-ethyl)carboxamide]
(13) Adenosine-5'-[(N-cyclobutyl)carboxamide]
(14) 2',3',$N^6$-tripropionyl-adenosine-5'-[(N-ethyl)-carboxamide]
(15) 2',3', $N^6,N^6$-tetra-acetyl adenosine-5'-[(N-cyclopropyl)carboxamide]
(16) Adenosine-5'-[(N-methoxy)carboxamide]
(17) 2',3'-(O-ethoxymethylene)-adenosin-5'-[N-ethyl)-carboxamide]
(18) 2-chloroadenosine-5'-[(N-ethyl)-carboxamide]
(19) 2-Amino adenosine-5'-[(N-ethyl)-carboxamide]
(20) Adenosine-5-[(N-ethyl)-carboxamide]-2',3'-carbonate
(21) 2',3'-0-(4-chlorobenzylidene)-adenosine-5'-[(N-ethyl)carboxamide]mono hydrochloride and compounds of formula 2:

(22) Adenosine-5'-[(N-ethyl)carboxamide]-N'-oxide; and
(23) Adenosine-5'-[(N-cyclopropyl)carboxamide]-N'-oxide.

In practicing the present method for controlling undesired animals, the active compound may be incorporated into a food complement with or without baits. The drug can, for example, be incorporated into a food complement and/or bait by any convenient manner, as for instance, by simply mixing in the case of solid materials and by dissolution or suspension in the case of liquid materials. Thus, for example, the lethal drug is admixed in corn, oats, rye, wheat, bran or grass, legumes, milk, meat, fish or other nutrients, as well as mixtures thereof, or together with conventional baits, e.g., sugar molasses, corn oil, peanut oil, peanut butter, bacon, lard, mutton, tallow, and the like, as well as mixtures thereof.

The amount of drug employed in the edible compositions of the present invention can vary considerably. In order to control or regulate the amount of the edible composition that will be consumed by each member of a group of undesired animals, it is preferred to use as large an amount of the control chemical in the composition as possible without causing the composition to be objectionable to the undesired animals. This amount, i.e., the highest concentration, will vary with the particular animal being controlled and with the type of bait being used. Ordinarily, the amount of the lethal drug varies from about 0.0001 to about 0.5 percent by weight of the novel edible composition. However, amounts above or below this range can be used, if desired, depending on such factors as the type of animal being controlled.

In the case of controlling coyotes, a toxic collar program may also be used according to the present invention. According to this program, a toxic collar is placed around the neck of the sheep or animal which the coyotes generally attack. The toxic collar is composed of plastic packets which each contain a toxicant, i.e., a lethal amount of a drug in a suitable carrier. In the process of attacking a sheep, or any other animal wearing such a collar, a coyote self-administers a lethal dose of the drug by biting into the packets of the collar.

The following examples further illustrate the present invention.

EXAMPLE 1

2',3'-(O-ethoxymethylene)-adenosine-4'-[(N-ethyl)carboxamide]

A mixture of adenosine-5'-(N-ethyl)carboxamide (3.0 g.) in dry DMF (40 ml.) containing ethyl orthoformate (6 ml.) was mixed with a solution of dry HCl (2.3 ml. of 5.6N solution of HCl in dry DMF). The clear solution was stirred (26 hours) at the room temperature.

At the end of this period, triethylamine (2 ml.) was added to the reaction mixture, stirred and filtered.

The filtrate was evaporated, and after the removal of triethylamine, DMF was distilled under high vacuum in a 40°–50° C. bath. The white solid residue was dissolved in a mixture of ethyl acetate:CHCl$_3$(4:1) and the solution was filtered and concentrated to give 3.0 g. of 2',3'-O-ethoxymethylene adenosine-4'-(N-ethyl) carboxamide, melting at 150°–151°.

Analysis Calcd. for $C_{15}H_{20}N_6O_5$: C, 49.44; H, 5.53; N, 23.06 Found: C, 48.90; H, 5.79; N, 22.67

EXAMPLE 2

2-Chloroadenosine-5'-(N-ethyl)carboxylate

An aqueous solution of KMnO$_4$ (2.2 g.; 0.014 mole); in 60 ml. H$_2$O was added dropwise (3.5 hours) to a stirred suspension of 2-chloro-2',3'-O-isopropylidene adenosine (1.5 g., 0.0045 mole) in water (320 ml.) containing KOH (0.784 g., 0.014 mole), at the room temperature. The reaction mixture was stirred for 20 hours, then decolorized by the dropwise addition of H$_2$O$_2$ (5 ml. of 30% H$_2$O$_2$ in 20 ml. of H$_2$O) at 5°–10° C. and filtered through celite. The colorless filtrate was concentrated in vacuo (at 35°–40° C.) to 20 ml. and acidified (pH 4) with HCl. The white precipitate was filtered, successively washed with water, acetone and ether to give 1.2 g. (75%) of 2-chloro-2',3'-O-isopropylidene adenosine-5'-carboxylic acid, melting at 262°–63° C., $R_f$ 0.72 (isopropanol—NH$_4$OH—H$_2$O; 7:1:2).

A mixture of 2-chloro-2',3'-O-isopropylidene adenosine-5'-carboxylic acid (1.2 g, 0.0033 mole) in 50% HCOOH (70 ml.) was stirred (1.5 hours) at 70°–80° C. The solution was evaporated under reduced pressure (at 30°–40° C.); residue diluted with water and evaporated again. This process was repeated several times until there was no odor of formic acid in the residue. The residue, 2-chloroadenosine-5'-carboxylic acid, (0.8 g., 80%) was dried overnight at 60° C., in vacuo over P$_2$O$_5$; m.p. >300° C., ir (KBr) 1710 cm$^{-1}$; $R_f$ 0.51 (isopropanol—NH$_4$OH—H$_2$O 7:1:2).

The dried 2-chloroadenosine-5'-carboxylic acid (0.70 g., 0.022 mole) was stirred in absolute ethanol (100 ml.) at 5° C. and SOCl$_2$ (0.8 ml.) was added dropwise. After a few minutes a clear solution was obtained, but about an hour later (at 5°–10° C.) there was separation of a solid. Stirring was continued overnight at the room temperature. The reaction mixture was then diluted with dry ether (50 ml.) and filtered to give 0.8 g. (95%) of a white powder melting at 132°–39° C. Recrystallization from ethanol-benzene gave the flocculent white ester (ir 1730 cm$^{-1}$, m.p. 150°–55° C. dec.); $R_f$ 0.76 (CHCl$_3$—MeOH; (6:1); NMR (DMSO—d$_6$)δ 8.73 (H$_8$), 7.36 (6—NH$_2$+2',3'—OH), 1.23

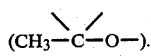

Mass spectra gave the molecular ion peak at m/e 343 and the fragmentation pattern was consistent with the structure of 2-chloro-adenosine-5'-(ethyl)-carboxylate.

Analysis Calcd, for C$_{12}$H$_{14}$ClN$_5$O$_5$.HCl: C, 37.91; H, 3.98; Cl, 18.65; N, 18.42; O, 21.04 Found: C, 37.61; H, 4.05; Cl, 18.66; N, 18.34; O, 21.10

EXAMPLE 3

2-Chloroadenosine-5'-(N-ethyl)carboxamide (18)

An aqueous solution of 2-chloro-adenosine-5'-(ethyl)-carboxylate was basified with aqueous NaHCO$_3$ and the precipitate was filtered, washed with water and dried overnight in vacuo over P$_2$O$_5$. The dried material (1.6 g.) was added to liquid ethyl amine (60 ml.) cooled in dry-ice. After stirring for three hours at $-20°$ C., the reaction mixture was slowly allowed to warm up to the room temperature and then left at this temperature for twenty hours. The solid residue left, was stirred with ethanol, filtered and washed with dry ether to give 1.5 g. (94%) of the amide, 2-chloroadenosine-5'-(N-ethyl)-carboxamide, melting at 245°–247° C. dec. After washing with boiling ethanol, the m.p. of the product was 250°–251° C., $R_f$ 0.29 (CHCl$_3$—MeOH; 6:1)

Analysis Calcd. for C$_{12}$H$_{15}$ClN$_6$O$_4$: C, 42.02; H, 4.41; N, 24.50 Found: C, 41.91; H, 4.47; N, 24.42

EXAMPLE 4

2-Amino-Adenosine-5'-(N-ethyl)carboxamide (19)

2,6-Diacetamido-9-(tri-O-acetyl-β-D-ribofuranosyl)-purine

Dry HCl gas was passed through a mixture of dry 1,2,3,5-tetra-O-acetyl-β-D-ribofuranoside (20.4 g, 0.064 mole) in anhydrous ether (400 ml.) at 5° C., until a clear solution was obtained (1¼ hours). The solution was stirred at the room temperature for 90 minutes and then evaporated in vacuo. The residual oil was mixed with CCl$_4$ and evaporation continued. This process was repeated a few times, under anhydrous conditions. The residual liquid was taken up in freshly distilled xylene and refluxed with chloromercuri-2,6-diacetamido purine (30 g., 0.064 mole, dried by keeping in vacuo for twenty-four hours over P$_2$O$_5$ and then by refluxing with xylene until no more water separated in the Dean-Stark receiver) for four hours and then left overnight at the room temperature. The residue was extracted several times with warm dry CHCl$_3$, and the extract was washed (as usual), dried and stirred with charcoal, filtered and evaporated in vacuo to give nearly colorless powder (16.0 g., 51.5%) instead of a glass; m.p. 87°–92° C., δmax (MeOH) in nm 226, 269, NMR (CDCl$_3$-d$_6$) δ9.8 (NH), 9.35 (NH), 8.35 (H$_8$), 7.3 (NH$_2$), 6–5 (2',3',5'—OH), 2.3 (CH$_3$-C=O).

2-Acetamido-2',3'-O-isopropylidene adenosine

The 2-acetamido-adenosine used in this preparation was prepared from 2,6-diacetamido-9-(tri-O-acetyl-β-D-ribofuranosyl)purine by the method described by Davoll and Lowy, J. Amer. Cham. Soc., 73, 1650 (1951). A suspension of 2-acetamido adenosine (7.3 g; 0.0225 mole) in dry acetone (1.5.1) was mixed with p-toluene sulfonic acid monohydrate (43 g., 0.0225 mole) and stirred. A clear solution which resulted immediately gave heavy precipitate in five minutes. After stirring for fifteen minutes at room temperature, solid NaHCO$_3$ (70 g.) was added and stirring was continued for another twenty-four hours. The solids were separated by filtration and filtrate was evaporated to dryness. The residue on trituration with ether gave 6.7 g. (82%) of 2-acetamido-2',3'-O-isopropylidene adenosine, melting at 197°–203° C.; $R_f$ 0.56 (CHCl$_3$—MeOH; 9:1); λmax (MeOH) in nm: 226; 271; NMR (DMSO-d$_6$)δ9.9 (NH), 8.25 (H$_8$), 7.3 (NH$_2$), 2.3 (CH$_3$CO), 1.3 & 1.5 (2CH$_3$).

2-Acetamido-2',3'-O-isopropylidene adenosine-5'-carboxylic acid

Powdered 2-acetamido-2',3'-O-isopropylidene adenosine (2.5 g., 0.00687 mole) was suspended in warm water (400 ml.) and cooled to room temperature. Aqueous KOH (1.15 g., 0.0206 mole in 30 ml. H$_2$O) was added, with stirring, followed by a slow addition (1.5 hour) of KMnO$_4$ (4.3 g. in 100 ml. H$_2$O) at room temperature. Excess KMnO$_4$ was destroyed by the dropwise addition of 20% H$_2$O$_2$ (at 5–10° C.) until there was no more pink color. The precipitated MnO$_2$ was removed by filtration through celite. The clear filtrate was brought to pH 7 to 7.5 and then evaporated to near dryness below 40° under reduced pressure. The pH was then adjusted to 5–6 by dilute HCl and the solution was evaporated to dryness under reduced pressure. The residue was repeatedly extracted with boiling absolute ethanol. The ethanol extract on evaporation gave 2.0 g. (77%) of 2-acetamido-2',3'-O-isopropylidene adenosine-5'-carboxylic acid having an indefinite melting point (160° C. . . 176° C. . . 197° C. dec.). In order to confirm the structure of the acid λmax (MeOH) in nm; 225, 271), it was converted into its ethyl ester as described below.

A mixture of 2-acetamido-2',3'-O-isopropylidene adenosine-5'-carboxylic acid (0.4 g., 0.00105 mole) in absolute ethanol (60 ml.) and SOCl$_2$ (0.5 ml.) at room temperature, was stirred for fifteen hours and then evaporated to dryness under reduced pressure below 30° C. The residue was dissolved in aqueous NaHCO3 solution at 10° C. and the basic solution was extracted successively with CHCl3 and ethyl acetate. The organic extracts were combined, dried and evaporated to dryness and recrystallized from absolute ethanol to give 0.64 g. (15%) of 2-acetamido-2',3'-O-isopropylidene adenosine-5'-(ethyl)-carboxylate melting at 221°-222° C. having the characteristic ir peak at 1740 cm$^{-1}$; λmax (MeOH) in nm 225, 271; NMR (DMSO-d6)δ 9.77 (NH), 8.16 (H8), 7.20 (NH2), 2.16 (CH3—CO), 1.53,

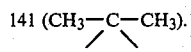

141 (CH3—C—CH3).

Analysis Calc. for $C_{17}H_{22}N_6O_6$: C, 50.24; H, 5.46; N, 20.68 Found: C, 50.31; H, 5.59; N, 20.88

2-Acetamido adenosine-5'-carboxylic acid

A solution of 2-acetamido-2',3'-O-isopropylidene adenosine-5'-carboxylic acid (2.0 g., 0.0053 mole) in 50% formic acid (80 ml.) was kept at 70° C. for seventy-five minutes and then evaporated to dryness under reduced pressure. The residue was mixed with a little water and evaporated again. This process was repeated a few times to give 0.8 g. (45%) of 2-acetamido adenosine-5'-carboxylic acid, melting at 295° C. Infra red spectra (KBr) showed the characteristic 1715 cm$^{-1}$ peak. The compound was insoluble in every solvent except aqueous base. λmax (0.1 N HCl+MeOH) in nm 215, 266.

Analysis Calcd. for $C_{12}H_{14}N_6O_6$: C, 42.61; H, 4.17; N, 24.84 Found: C, 41.83; H, 4.40; N, 24.59

2-Amino adenosine-5'-carboxylic acid

A mixture of 2-acetamido-2',3'-O-isopropylidene adenosine-5'-carboxylic acid (1.0 g., 0.0026 mole) in 1N HCl was kept at 60°-65° C. for thirty minutes. The reaction mixture was cooled, then basified with 50% NaOH and acidified with acetic acid. The precipitate was filtered, washed successively with water and ethanol to give 0.2 g. (23%; m.p. 228° C.) of 2-amino-adenosine-5'-carboxylic acid; λmax (MeOH) in nm 223, 248 and 278.

2-Amino adenosine-5'-(ethyl) carboxylate

Thionyl chloride (2.5 ml.) was added dropwise to a suspension of 2-acetamido-adenosine-5'-carboxylic acid (2.5 g., 0.0074 mole) in absolute ethanol (120 ml.) at 0° C. After an hour at 0° C., the reaction mixture was stirred overnight at the room temperature. The mixture was cooled, diluted with ether and filtered to give 1.9 g. of 2-amino adenosine-5'-(ethyl) carboxylate as a hydrochloride salt. The salt was dissolved in water and basified with NaHCO3 solution, filtered, washed successively with water, ethanol, ether and dried in vacuo over P2O5 to give 1.2 g. (44%) of 2-amino-adenosine-5'-(ethyl) carboxylate as a monohydrate melting at 215°-216° C. dec.; ir (KBr) 1740 cm$^{-1}$; λmax (meOH) in 221, 258, 278; NMR (DMSO-d6)δ 8.08 (H8), 6.86 (NH2), 5.8 (NH2, 2',3'-OH),

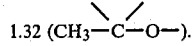

1.32 (CH3—C—O—).

A molecular ion peak at 324 and a fragment at m/e 150 confirmed the structure of 2-amino adenosine-5'-(ethyl) carboxylate.

Analysis Calcd. for $C_{12}H_{16}N_6O_5.H_2O$: C, 42.11; H, 5.30; N, 24.55 Found: C, 42.07; H, 4.78; N, 24.55

2-Acetamido adenosine-5'-(ethyl) carboxylate

In the preceding reaction, the mother liquor, after the removal of 1.2 g. of 2-amino adenosine-5'-(ethyl) carboxylate, was evaporated to dryness at 30° C. under reduced pressure. The residue was washed with ether and then stirred with aqueous NaHCO3 solution. The insoluble material, 2-acetamido adenosine-5'-(ethyl) carboxylate (0.147 g., m.p. 252°-255° C. dec.) had the characteristic ir peaks: 1745 cm$^{-1}$, 1720 cm$^{-1}$ and 1650 cm$^{-1}$; λmax (MeOH) in nm 225, 271; R$_f$ 0.76 (n-butanol-acetic acid-H2O; 5:2:3); NMR (DMSO-d6)δ9.89 (NH), 8.23 (H8), 7.23 (NH2), 6.0–5.5 (2',3'-OH),

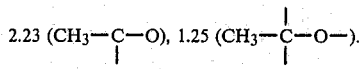

2.23 (CH3—C—O), 1.25 (CH3—C—O—).

Analysis Calcd. for $C_{14}H_{18}N_6O_6$: C, 45.90; H, 4.95; N, 22.94 Found: C, 45.59; H, 4.96; N, 23.06

2-Amino adenosine-5'-(N-ethyl) carboxamide (19)

The ester, 2-amino adenosine-5'-(ethyl) carboxylate, (1 g., 0.00292 mole) was added to liquid monothylamine (≈20 ml.). The clear solution was allowed to warm up to the room temperature and stirred under N2 until the excess of the amine evaporated off. Absolute ethanol was added to the residue and the mixture was evaporated in vacuo. The residue, on two recrystallization from absolute ethanol, gave 1.0 g. (m.p. 113°. . . 120°-23° dec) of the product (19).

Analysis Calcd. for $C_{12}H_{17}N_7O_4.0.5EtOH$: C, 44.11; H, 5.92; O, 21.15 Found: C, 44.07; H, 6.14; O, 21.21

The structure was confirmed by NMR.

EXAMPLE 5

Adenoisine-5'-(N-ethyl) carboxamide

2',3'-isopropylidene adenosine-5'-carboxylic acid and thionylchloride was stirred with excess of dry liquid ethyl amine at −50° to −35° C. The clear orange-red solution was slowly allowed to warm up to the room temperature, and then kept for fifteen hours at the room temperature under anhydrous conditions. At the end of the period (when most of the excess ethyl amine had evaporated off) the residue was stirred with cold aqueous NaHCO3 solution at 0° C., filtered and washed with a small amount of ice-cold water to give 3.1 g. of 2',3'-O-isopropylidene adenosine-5'-(N-ethyl) carboxamide; m.p. 225°-227°); R$_f$ 0.72 (silica gel), system; n-BuOH:-H2O:NH OH (86:14:5). The crude amide was heated with 80 ml. 1N HCl at 65° for forty-five minutes. The acidic solution was cooled, basified with NaHCO3 and evaporated to dryness under reduced pressure. The residue was recrystallized twice from ethanol and finally from a small amount of water. The white crystalline product was dried (70°-80°) in vacuo over P2O5 for forty-eight hours to give 0.1 g. (32%) of adenosine-5'-(N-ethyl) carboxamide (5), which melted slowly above 136° and solidified again at 148°-150° and finally melted again at 246°-247°; [α]$_D^{26}$ −163° (c, 0.92 in 1N HCl); R$_f$ 0.51 (silica gel), system; n-BuOH:H2O; NH4OH (86:14:5). Elemental analysis and NMR data confirmed the identity of the product (5).

EXAMPLE 6

Adenosine-5'-[(N-ethyl)carboxamide]-2',3'-carbonate (20)

A mixture of adenosine-5'-(N-ethyl) carboxamide (5) (2.0 g., 0.0065 mole) and 1,1'-carbonyldiimidazole (4.0 g., 0.024 mole) in dry DMF (35 mole) was stirred at the room temperature. After four hours, the reaction mixture was diluted with ether containing a little petroleum ether (30°–60°). The gummy precipitate was triturated with cold ethanol and the product (m.p. 226°–230°) was filtered. Two recrystallizations from ethyl acetate gave 1.0 g. of the product (20) melting at 235°–236° C.

Analysis Calcd. for $C_{13}H_{14}N_6O_5$: C, 46.71; H, 4.22; N, 25.14 Found: C, 46.40; H, 4.23; N, 24.97

EXAMPLE 7

Adenosine-5'-(N-cyclopropyl) carboxamide $N^1$-oxide (23)

Hydrogen peroxide (11 ml. of 30% $H_2O_2$) was added to a suspension of 3.2 g. of adenosine-5'-(N-cyclopropyl) carboxamide (7, prepared as described before) in glacial acetic acid (100 ml.). The clear solution was left at the room temperature for four days. At the end of this period, the mixture was cooled to 0° C. stirred with 5% Pd/C (1.0 g.) for 0.5 hours and then at 10°–15° C. for another thirty minutes, and finally filtered through celite and charcoal. The residue was washed with methanol and the filtrate was concentrated under reduced pressure. The residual liquid was successively diluted with methanol, methanol and benzene, benzene and was evaporated each time under reduced pressure to give a viscous mass. Trituration of the latter with acetone/ether gave the product as a pinkish white solid.

Two recrystallizations from ethanol/benzene gave 2.5 g. of adenosine-5'-(N-cyclopropyl) carboxamide-$N^1$-oxide melting at 195°–197°; $[\alpha]_D^{26} -10+11°$ (c=0.95 in 1N.HCl).

Analysis Calcd. for $C_{13}H_{16}N_6O_5$: C, 46.49; H, 4.76; N, 25.00 Found: C, 46.09; H, 4.66; N, 24.44

The structure was confirmed by NMR.

EXAMPLE 8

Adenosine-5'-(N-ethyl) carboxamide-$N^1$-oxide (22)

Adenosine-5'-(N-ethyl) carboxamide-$N^1$-oxide was prepared according to the method described above in Example 7. Starting from adenosine-5'-(N-ethyl) carboxamide (3.1 g.), in glacial acetic acid and 30% $H_2O_2$, 1.8 g. (57%) of the corresponding $N^1$-oxide was obtained, melting at 237°–238°.

Recrystallization from ethanol/ether gave pure adenosine-5'-(N-ethyl) carboxamide-$N^1$-oxide melting at first over 185°, resolidified and then melts again at 240° decomp.; $R_f$ 0.23 (n-BuOH:$H_2O$:$NH_4OH$ — 86:14:5).

Analysis Calcd. for $C_{12}H_{16}N_6O_5$: C, 44.44; H, 4.93; O, 24.69 Found: C, 44.08; H, 5.17; O, 24.31

EXAMPLE 9

$N^6$-Methyl adenosine-5'-(N-ethyl) carboxamide (8)

A solution of 2',3'-O-isopropylidene adenosine-5'-carboxylic acid (9.6 g., 0.03 mole) at 60°–70° in dry DMF (600 ml.) was cooled to 30°, methyl iodide (21.3 g., 0.15 mole) was added and the mixture was stirred under nitrogen. After six days at 30° C., the reaction mixture was poured into five liters of 1:5 mixture of ether:petroleum ether (30°–60°). The mixture was stirred and then left overnight at 0°–10°. The supernatant liquid was decanted off the residue and triturated several times with petroleum ether. Finally, the washed residue was dissolved in water (300 ml.), basified wth concentrated $NH_4OH$ (15 ml.) and heated over a steambath for two hours. The reaction mixture was then concentrated (150 ml. or less) under reduced pressure, cooled, acidified (pH 4–5) with glacial acetic acid. The precipitated $N^6$-methyl-2',3'-O-isopropylidene adenoisine-5'-carboxylic acid was filtered, washed with a small amount of cold water and dried at 60° in vacuo over $P_2O_5$ for eight hours.

Yield 7.0 g. (70%; m.p. 223°–25° dec.); $R_f$0.20 (system; n-BuOH:AcOH:water; 4:1:5).

The dried $N^6$-methyl-2',3'-O-isopropylidene adenosine-5'-carboxylic (4.5 g.) was added, portionwide, to stirred $SOCl_2$ (40 ml.) at 0° C. After the addition was completed, the reaction mixture was stirred for two hours at the room temperature. The clear yellow reaction solution was then poured onto well stirred ether (400 ml.). The precipitated $N^6$-methyl-2',3'-O-isopropylidene adenosine-5'-carboxylic acid chloride was filtered, washed with plenty of dry ether (until free from $SOCl_2$) and then added to an excess of liquid ethyl amine at −30° C. The reaction mixture was stirred (24 hours) and was allowed to warm up slowly to the room temperature. The reaction mixture was evaporated to dryness, basified with aqueous $NaHCO_3$ solution and extracted with $CHCl_3$. The dry $CHCl_3$ extract was evaporated to give 2.9 g. of $N^6$-methyl-2',3'-O-isopropylidene adenosine-5'-(N-ethyl) carboxamide, melting at 80° with foaming; $R_f$0.59 (n-butanol-conc. $NH_4OH$: $H_2O$; 86:5:14).

The pure $N^6$-methyl-2',3'-O-isopropylidine adenosine-5'-(N-ethyl)carboxamide (2.9 g.) was mixed with formic acid (60 ml. of 50%) and kept at the room temperature until 14 days, when the hydrolysis was completed (TLC). At the end of this period, the reaction mixture was evaporated to dryness. The residue was triturated several times with ether and then dissolved in absolute ethanol and filtered (norit). The filtrate, on dilution with ether gave some precipitate. The precipitate was discarded, the filtrate was evaporated to dryness and the residue was dried in vacuo at the room temperature over $P_2O_5$ for 72 hours to give pure $N^6$-methyl adenosine-5'-(N-ethyl)-carboxamide (8) in 35% yield; m.p. 130°–31°; $[\alpha]_D^{26} =23° \pm 1.1°$ (c=0.17 in 1N.HCl); $R_f$0.52 (n-BuOH:$NH_4OH$:$H_2O$; 86:5:14).

Analysis Calcd. for $C_{13}H_{18}N_6O_4$: C, 48.49; H, 5.62; N, 26.06; O, 19.83 Found: C, 47.88; H, 5.96; N, 26.89; O, 20.24

The structure was confirmed by the NMR spectra.

EXAMPLE 10

$N^6$-Methyl adenosine-5'-(N-cyclopropyl) carboxamide (9)

$N^6$-Methyl adenosine-5'-(N-cyclopropyl) carboxamide (9) was prepared according to the method described above, in Example 9. Thus, the intermediate, $N^6$-methyl-2',3'-O-isopropylidene adenosine-5'-(N-cyclopropyl) carboxamide was obtained from $N^6$-methyl-2',3'-O-ixopropylidene adenosine-5'-carboxylic acid in 52% yield, melting at 85°–88° (THF petroleum ether); $R_f$0.63 [same system as for N -methyl-2',3'- O-isopropylidene adenosine-5'-(N-ethyl)carboxamide].

The carboxamide was hydrolyzed for 12 days (TLC) with 50% HCOOH, as before. The residue, after evaporation of the reaction mixture, was purified twice by solution in acetone with the help of a little ethanol (norit) to give pure N -methyl adenosine-5'-(N-cyclopropyl) carboxamide (9) in 28% yield, melting at 128°–133° (foams); $R_f$ 0.53 same as above system. The compound (9) had the desired IR and NMR spectra.

Analysis Calcd. for $C_{14}H_{18}N_6O_4$: C, 50.29; H, 5.42; N, 25.14; O, 19.14 Found: C, 50.08; H, 5.73; N, 24.90; O, 19.25

EXAMPLE 11

Adenosine-5'-(β-chloroethyl) carboxylate

Thionyl chloride (4.5 ml.) was added to a stirred suspension of adenosine-5'-carboxylic acid (14.0 g., 0.05 mole) in re-distilled β-chloroethanol (150 ml.) at 10°–15° C. After thirty minutes at this temperature, the mixture was stirred at the room temperature for sixteen hours. At the end of this period, ether was added to precipitate adenosine-5'-(β-chloroethyl) carboxylate as HCl salt. The crude hydrochloride salt of adenosine-5'-(β-chloroethyl) carboxylate was stirred with aqueous $NaHCO_3$, filtered, washed successively with water, acetone and ether. The dried residue (11.0 g., 65%, m.p. 205°–206° C.) was recrystallized from acetone to give the analytically pure ester with no substantial change in melting point. $[\alpha]_D^{26}$ −35±2.2° C. (c, 0.96 in 1N.HCl).

Analysis Calcd. for $C_{12}H_{14}ClN_5O_5.1/2H_2O$: C, 40.08; H, 4.25; Cl, 10.07; N, 20.00; O, 25.25 Found: C, 39.79; H, 4.42; Cl, 10.20; N, 20.78; O, 25.11

EXAMPLE 12

Adenosine-5'-(N-cyclobutyl) carboxamide (13)

Adenosine-5'-(β-chloroethyl) carboxylate (3.0 g.) was added to cyclobutylamine (10 ml.) in $N_2$ atmosphere. After the exothermic reaction was over, the mixture was refluxed for thirty minutes, and then the solvent was evaporated under reduced pressure. The oily residue was taken up in hot absolute ethanol, filtered (norit) and the filtrate on cooling gave 2.5 g. (86%) of the adenosine-5'-(N-cyclobutyl) carboxamide. Recrystallization from absolute ethanol gave pure adenosine-5'-(N-cyclobutyl) carboxamide; m.p. 234°–235°.

Analysis Calcd. for $C_{14}H_{18}N_6O_4$: C, 50.32; H, 5.42; N, 25.14 Found: C, 50.52; H, 5.56; N, 24.72

EXAMPLE 13

2',3'-O-(4-Chlorobenzylidene) adenosine-5'-(N-ethyl) carboxamide monohydrochloride (21)

A mixture of adenosine-5'-(N-ethyl) carboxamide (2 g.; 0.0065 mole) and p-chloro benzaldehyde dimethyl acetal (10 ml.) in dioxane (100 ml.) was gently refluxed using Barrett water separator trap. The temperature in the reflux condenser was adjusted such that any methanol formed would slowly distil off. After 2¼ hours, dry DMF (10 ml.) was added to the reaction mixture, followed by another 10 ml. of DMF after 5¼ hours, while refluxing was continued. A 4N-HCl dioxane solution (4 ml.) was then added to the clear hot reaction mixture and allowed to stand. After three days at the room temperature, the waxy solid was filtered (1.3 g.; m.p. 153°–157° dec.). The filtrate, on adding ether, gave some more product (0.43 g.). Recrystallization from ethanol gave the pure 2',3'-O-(4-chlorobenzylidene) adenosine-5'-(N-ethyl) carboxamide as a mono hydrochloride, melting at 163°–166° dec.; $R_f$ 0.73 (system: n-butanol saturated with water).

Analysis Calcd. for $C_{19}H_{20}Cl_2N_6O_4$: Cl, 15.17; N, 17.98; O, 13.70 Found: Cl, 14.93; N, 17.77; O, 13.78

Nmr spectra confirmed the structure of the compound.

We claim:

1. A method of eliminating undesired animals selected from the group consisting of rodents, coyotes and birds which are economically or socially destructive to man, which method comprises administering to said animals a lethal dose of a compound represented by the formulae

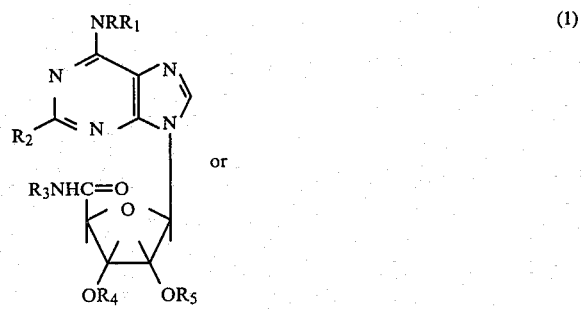

or

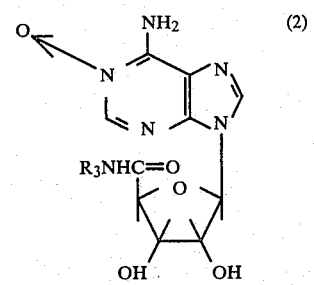

wherein R is H, loweralkyl of 1 to 6 carbon atoms or acetyl; $R_1$ is H or acetyl; $R_2$ is H, Cl or $NH_2$; $R_3$ is H, loweralkyl of 1 to 6 carbon atoms, alkoxy of no more than 6 carbon atoms, cycloalkyl of 3 to 8 carbon atoms or hydroxyalkyl of 1 to 6 carbon atoms; $R_4$ and $R_5$ are each H, acetyl or propionyl, or when taken together form a p-chlorobenzylidene, a carbonate or an ethoxymethylene moiety; in a suitable carrier.

2. A method according to claim 1, wherein said lethal dose ranges from 1 to 100 mg./kg. of body weight.

3. A method according to claim 1, wherein said compound is represented by formula 1; each of R, $R_1$, $R_2$, $R_4$ and $R_5$ is H; and $R_3$ is —$CH_2CH_3$.

4. A method according to claim 1, wherein said compound is represented by formula 1; each of R, $R_1$, $R_2$, $R_4$ and $R_5$ is H; and $R_3$ is

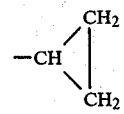

5. A method according to claim 1, wherein said compound is represented by formula 1; each of R, $R_1$, $R_2$, $R_4$ and $R_5$ is H; and $R_3$ is —$CH(CH_3)_2$.

6. A method according to claim 1, wherein said compound is represented by formula 1; each of R, $R_1$ and $R_2$ is H; $R_3$ is

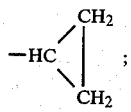

and each of $R_4$ and $R_5$ is acetyl.

7. A method according to claim 1, wherein said compound is represented by formula 1; each of R, $R_1$ and $R_2$ is H; $R_3$ is —$CH_2CH_3$; and each of $R_4$ and $R_5$ is acetyl.

8. A method according to claim 1, wherein said compound is represented by formula 1; each of R, $R_1$ and $R_2$ is H; $R_3$ is cyclobutyl; and each of $R_4$ and $R_5$ is acetyl.

9. A method according to claim 1, wherein said compound is represented by formula 1; each of R, $R_1$ and $R_2$ is H; $R_3$ is —$CH_2CH_3$; and each of $R_4$ and $R_5$ is propionyl.

10. A method according to claim 1, wherein said compound is represented by formula 1; each of R, $R_1$, and $R_2$ is H; $R_3$ is —$CH_2CH_3$; and $R_4$ and $R_5$ together are

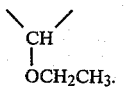

11. A method according to claim 1, wherein said compound is represented by formula 1; each of R, $R_1$ and $R_2$ is H; $R_3$ is —$CH_2CH_3$; and $R_4$ and $R_5$ together are

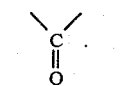

12. A method according to claim 1 wherein R is H, $CH_3$ or acetyl, $R_1$ is H or acetyl, $R_2$ is H, Cl or $NH_2$, $R_3$ is H, $CH_3$, —$CH_2CH_3$—$CH_2CH_2OH$,

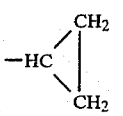

or ethoxy, and $R_4$ and $R_5$ are each H, acetyl, or

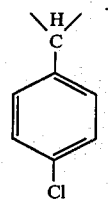

13. A method according to claim 1 wherein said compound is represented by formula 2 and $R_3$ is —$CH_2CH_3$ or

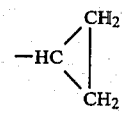

14. A compound of the formula

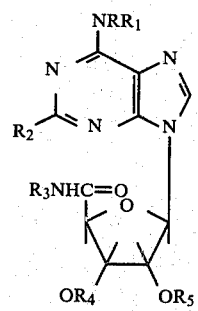

wherein R, $R_1$, $R_4$ and $R_5$ are each H, $R_2$ is Cl or $NH_2$ and $R_3$ is —$CH_2CH_3$.

15. A compound of the formula

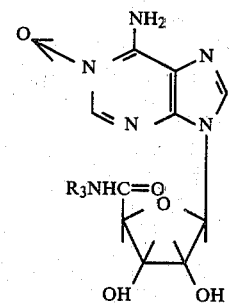

wherein $R_3$ is —$CH_2CH_3$ or

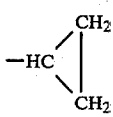

* * * * *